United States Patent
Ho et al.

(10) Patent No.: US 10,594,166 B2
(45) Date of Patent: Mar. 17, 2020

(54) PLANAR IMMERSION LENS WITH METASURFACES

(71) Applicant: THE BOARD OF TRUSTEES OF THE LELAND STANFORD JUNIOR UNIVERSITY, Stanford, CA (US)

(72) Inventors: John S. Y. Ho, Stanford, CA (US); Ada Shuk Yan Poon, Redwood City, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 179 days.

(21) Appl. No.: 15/514,270

(22) PCT Filed: Sep. 28, 2015

(86) PCT No.: PCT/US2015/052642
§ 371 (c)(1),
(2) Date: Mar. 24, 2017

(87) PCT Pub. No.: WO2016/049629
PCT Pub. Date: Mar. 31, 2016

(65) Prior Publication Data
US 2017/0250577 A1    Aug. 31, 2017

Related U.S. Application Data

(60) Provisional application No. 62/056,223, filed on Sep. 26, 2014.

(51) Int. Cl.
*G02B 1/00* (2006.01)
*H02J 50/30* (2016.01)
(Continued)

(52) U.S. Cl.
CPC ............ *H02J 50/30* (2016.02); *A61B 5/0031* (2013.01); *A61B 5/686* (2013.01); *A61N 1/3787* (2013.01);
(Continued)

(58) Field of Classification Search
CPC ......... H02J 50/30; H02J 50/27; A61B 5/0031; A61B 5/686; A61B 2560/0219;
(Continued)

(56) References Cited

U.S. PATENT DOCUMENTS 8,823,214 B2 * 9/2014 Liu .................. H01F 38/14
307/104
9,564,777 B2 * 2/2017 Yeh .................. A61B 18/18
(Continued)

OTHER PUBLICATIONS

Andrea Di Falco, Yang Zhao, and Andrea Alu, "Optical metasurfaces with robust angular response on flexible substrates", Appl. Phys. Lett. 99, 163110 (2011); pp. 1631101-1631103, https://doi.org/10.1063/1.3655332, Published Online: Oct. 21, 2011, (Year: 2011).*
(Continued)

Primary Examiner — William R Alexander
(74) Attorney, Agent, or Firm — Shay Glenn LLP

(57) ABSTRACT

A planar immersion lens can include any number of features. A planar immersion lens can be configured to control a phase profile of an incident wave by modulating the incident wave with sub-wavelength structures of varying impedances. The planar immersion lens can also be directly excited, with electronics or other subwavelength sources coupled to the planar immersion lens, to generate a wave with the desired phase profile. The planar immersion lens can include a plurality of metallic elements and passive elements disposed over a substrate. The passive elements can be selected, based on both the intrinsic and mutual impedances of the elements, to shape the spatial phase profile of the incident wave within this phase range. The phase gradient can be introduced along the incident material/refractive material interface to focus the incident wave into the refractive material having wave components at or beyond the critical angle. Methods are also provided.

17 Claims, 5 Drawing Sheets

(51) Int. Cl.
| | |
|---|---|
| *A61N 1/378* | (2006.01) |
| *G02B 6/124* | (2006.01) |
| *A61B 5/00* | (2006.01) |
| *H02J 50/27* | (2016.01) |
| *G02B 27/56* | (2006.01) |
| *H01Q 1/24* | (2006.01) |
| *H01Q 3/26* | (2006.01) |
| *H01Q 21/22* | (2006.01) |

(52) U.S. Cl.
CPC ............ *G02B 1/002* (2013.01); *G02B 6/1245* (2013.01); *G02B 27/56* (2013.01); *H01Q 1/248* (2013.01); *H01Q 3/2676* (2013.01); *H01Q 21/22* (2013.01); *H02J 50/27* (2016.02); *A61B 2560/0219* (2013.01)

(58) Field of Classification Search
CPC .... A61N 1/3787; G02B 1/002; G02B 1/1245; G02B 27/56; H01Q 1/248; H01Q 3/2676; H01Q 21/22
USPC ......................................................... 359/642
See application file for complete search history.

(56) References Cited

U.S. PATENT DOCUMENTS

| | | | |
|---|---|---|---|
| 2004/0066251 A1 | 4/2004 | Eleftheriades et al. | |
| 2010/0033389 A1 | 2/2010 | Yonak et al. | |
| 2011/0133568 A1 | 6/2011 | Wang et al. | |
| 2011/0248673 A1 | 10/2011 | Aerts et al. | |
| 2012/0328240 A1 | 12/2012 | Ma et al. | |
| 2013/0229704 A1 | 9/2013 | Smolyaninov | |
| 2014/0058506 A1* | 2/2014 | Tai ...................... | A61N 1/0543 623/4.1 |
| 2014/0159479 A1 | 6/2014 | Nomura et al. | |
| 2016/0306157 A1* | 10/2016 | Rho ...................... | G02B 21/361 |
| 2016/0344238 A1* | 11/2016 | Yeh .................... | A61N 1/37229 |
| 2016/0344240 A1* | 11/2016 | Yeh .................... | A61N 1/3787 |

OTHER PUBLICATIONS

Aieta et al.; Aberration-free ultrathin flat lenses and axicons at telecom wavelengths based on plasmonic metasurfaces; 12(9); pp. 4932-4936; Aug. 21, 2012.
Chen et al.; Dual-polarity plasmonic metalens for visible light; Nature Communications; 3(1198); (Manuscript copy, 6 pages); Nov. 13, 2012.
Engheta et al.; Circuits with light at nanoscales: Optical nanocircuits inspired by metamaterials; Science; 317(5845); pp. 1698-1702; Sep. 21, 2007.
Gabriel et al.; The dielectric properties of biological tissues: III. Parametric models for the dielectric spectrum of tissues; Physics in Medicine and Biology; 41(11); pp. 2271-2293; Nov. 1996.
Genevet et al.; Ultra-thin plasmonic optical vortex plate based on phase discontinuities; Applied Physics Letters; 100(1): 013101; (Manuscript copy,4 pages); Jan. 2, 2012.
Ghislain et al.; Near-field photolithography with a solid immersion lens; Applied Physics Letters; 74(4); pp. 501-503; Jan. 25, 1999.
Grbic et al.; Near-field plates: Metamaterial surfaces/arrays for subwavelength focusing and probing; Proceedings of the IEEE; 99(10); pp. 1806-1815; Oct. 2011.
Grbic et al.; Near-field plates: Subdiffraction focusing with patterned surfaces; Science; 320(5875); pp. 511-513; Apr. 25, 2008.
Ho et al.; Wireless power transfer to deep-tissue microimplants; Proceedings of the National Academy of Sciences; 111(22); pp. 7974-7979; Jun. 3, 2014.
Huang et al.; Three-dimensional optical holography using a plasmonic metasurface; Nature Communications; 4(2808); (Manuscript copy; 8 pages); Nov. 15, 2013.
Imani et al.; Planar near-field plates; IEEE Transactions on Antennas and Propagation; 61(11); pp. 5425-5434; Nov. 2013.
Kildishev et al.; Planar photonics with metasurfaces; Science 339(6125); p. 1232009; (Manuscript copy, 9 pages); Mar. 15, 2013.
Kim et al.; Epidermal electronics; Science; 333(6044); pp. 838-843; Aug. 12, 2011.
Kim et al.; Midfield wireless powering of subwavelength autonomous devices; Physical Review Letters; 110(20); p. 203905; (Manuscript copy, 5 pages); May 17, 2013.
Lerosey et al. Time reversal of electromagnetic waves; Physical Review Letters; 92(19); p. 193904; (Manuscript copy, 3 pages); May 14, 2004.
Li et al.; Flat metasurfaces to focus electromagnetic waves in reflection geometry; Optics Letters; 37(23); pp. 4940-4942; Dec. 1, 2012.
Ling et al.; Focusing of electromagnetic waves through a dielectric interface; JOSA A; 1(9); pp. 965-973; Sep. 1, 1984.
Mansfield et al.; Solid immersion microscope; Applied Physics Letters; 57(24); pp. 2615-2616; Dec. 10, 1990.
Milster et al.; Roles of propagating and evanescent waves in solid immersion lens systems; Applied Optics; 38(23); pp. 5046-5057; Aug. 10, 1999.
Monticone et al.; Full control of nanoscale optical transmission with a composite metascreen; Physical Review Letters; 110(20); p. 203903; (Manuscript copy; 5 pages); May 14, 2013.
Ni et al.; Broadband light bending with plasmonic nanoantennas; Science; 335(6067); p. 427; Jan. 27, 2012.
Ni et al.; Metasurface holograms for visible light; Nature Communications; 4(2807); (Manuscript copy, 6 pages); Nov. 15, 2013.
Pfeiffer et al.; Metamaterial huygens' surfaces: Tailoring wave fronts with reflectionless sheets; Physical Review Letters; 110(19); p. 197401; (Manuscript copy, 5 pages); May 6, 2013.
Sendur et al.; Near-field radiation from a ridge waveguide transducer in the vicinity of a solid immersion lens; Physical Review Letters; 94(4); pp. 043901; (Manuscript copy, 4 pages); Jan. 31, 2005.
Sun et al.; Experimental realization of optical lumped nanocircuits at infrared wavelengths; Nature Materials; 11(3); pp. 208-212; Mar. 1, 2012.
Sun et al.; Gradient-index meta-surfaces as a bridge linking propagating waves and surface waves; Nature Materials; 11(5); pp. 426-431; (Manuscript copy, 7 pages); May 1, 2012.
Sun et al.; High-efficiency broadband anomalous reflection by gradient meta-surfaces; Nano Letters; 12(12); pp. 6223-6229; Dec. 3, 2012.
Tanter et al.; Time reversal and the inverse filter; Journal of the Acoustical Society of America; 108(1); pp. 223-234; Jul. 2000.
Terris et al.; Near-field optical data storage using a solid immersion lens; Applied Physics Letters; 65(4); pp. 388-390; Jul. 25, 1994.
Wiersma et al.; Comparison of different theories for focusing through a plane interface; JOSA A; 14(7); pp. 1482-1490; Jul. 1, 1997.
Wiersma et al.; Defocusing of a converging electromagnetic wave by a plane dielectric interface; JOSA A; 13(2); pp. 320-325; Feb. 1, 1996.
Yu et al.; Flat optics with designer metasurfaces; Nature Materials; 13(2); pp. 139-150; Feb. 1, 2014.
Yu et al.; Light propagation with phase discontinuities: Generalized laws of reflection and refraction; Science; 334(6054); pp. 333-337; Oct. 21, 2011.
Ho et al.; Planar immersion lens with metasurfaces; Physical Review Review B; 91(12); 8 pages, DOI: 10.1103/PhysRevB.91. 125145; Mar. 30, 2015.
Verslegers et al.; Planar metallic nanoscale slit lenses for angle compensation; Applied Physics Letters; 95(7); 3 pages; DOI: 10.1063/1.3211875; Aug. 17, 2009.
Zhang et al.; On the point-matching method for solving electromagnetic radiation problems; IEEE; In 2013 IEEE Antennas and Propagation Society International Symposium (APSURSI); pp. 1526-1527; Jul. 7, 2013.

\* cited by examiner

PLANAR IMMERSION LENS WITH METASURFACES

CROSS REFERENCE TO RELATED APPLICATIONS

This application claims the benefit of U.S. Provisional Appln. No. 62/056,223, filed Sep. 26, 2014, titled "Planar Immersion Lens with Metasurfaces", which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure is related generally to wireless power transfer. More specifically, the present disclosure relates generally to systems and methods of focusing electromagnetic waves from one material into another material having a higher refractive index, specifically using flat passive devices.

BACKGROUND

Systems and methods that supply power without electrical wiring are sometimes referred to as wireless energy transmission (WET). Wireless energy transmission greatly expands the types of applications for electrically powered devices. Implantable medical devices typically require an internal power source able to supply adequate power for the reasonable lifetime of the device or an electrical cable that traverses the skin.

More recently there has been an emphasis on systems that supply power to an implanted device without using transcutaneous wiring, sometimes referred to as a Transcutaneous Energy Transfer System (TETS). Frequently energy transfer is accomplished using two magnetically coupled coils set up like a transformer so power is transferred magnetically across the skin. Conventional systems are relatively sensitive to variations in position and alignment of the coils, typically requiring the coils to be physically close together and well aligned.

Existing systems that transmit power wirelessly based on magnetic fields typically operate in the near-field only, where the separation of the transmitter and receiver coils is less than or equal to the dimension of the coils.

Wireless powering has long been of interest for enhancing the function of implantable electronics, beginning in the early 1960's with experiments in transporting electromagnetic energy across the chest wall. Drawing conceptually on schemes for transferring power over air through objects coupled in the near-field, early manifestations involved bulky coils tether to vacuum tube power supplies or battery cells that posed severe challenges for long-term operation in the body. Advances in semiconductor technology have since enabled sophisticated devices that incorporate sensing and stimulation capabilities within cellular-scale dimensions. Nearly all existing systems, however, continue to require large structures for energy storage or harvesting, often several centimeters in the largest dimension with overall size, weight, and efficiency characteristics that constrain opportunities for integration into the body.

Near-field approaches rely on strong coupling occurring between objects with matched electrical characteristics, such as resonances and impedances. These near-field approaches do not generalize easily to geometries with extreme size asymmetry, while far-field transfer is limited by absorption over surfaces of the body.

When electromagnetic radiation is focused from air into a material such as tissue, refraction at the air-material interface determines the diffraction limit. Conventional lenses, placed in the far field of the interface, control only propagating wave components in air. As a result, their focusing resolution in material is diffraction-limited at the free-space wavelength $\lambda$ because higher-wave-vector components in material cannot be accessed by far-field light. These high-wave-vector components correspond to plane waves propagating at angles greater than the critical angle, which are trapped in the material by total internal reflection.

A critical or "forbidden" angle is it is the largest angle of incidence for which refraction can still occur. Prior optical methods for accessing these "forbidden" angles of refraction rely on solid immersion lenses: semispherical domes of high-index material placed at or near the air-material interface. This capability enables radiation to be focused to a spot much smaller than the free-space wavelength, with a diffraction-limited resolution set by the material wavelength $\sim\lambda/n$.

In the radio-frequency regime, active devices have also been used to focus radiation from air into material. These systems generally involve phased arrays, in which many active radio-frequency components are used to generate the prescribed spatial phase profiles. These components can be bulky and require additional power supplies.

SUMMARY

A method for focusing electromagnetic radiation from an incident medium into a refractive medium is provided, comprising the steps of generating an incident electromagnetic wave across a surface of a planar immersion lens in the incident medium, and controlling a phase profile of the incident electromagnetic wave with the planar immersion lens to focus the incident electromagnetic wave into the refractive medium including wave components at or beyond a critical angle.

In some embodiments, the critical angle is an angle of incidence above which total internal reflection in the incident medium would occur without the planar immersion lens.

In one embodiment, the refractive medium has a higher refractive index than the incident medium.

In some embodiments, the controlling step further comprises controlling an arbitrary phase profile on the incident electromagnetic wave by modulating the incident electromagnetic wave with sub-wavelength structures of the planar immersion lens.

In one specific embodiment, the sub-wavelength structures comprise a plurality of metallic strips and passive elements. In other embodiments, the passive elements comprise resistors, capacitors, and/or inductors.

A method for transmitting wireless power from an incident medium into a refractive medium is provided, comprising the steps of generating an incident electromagnetic wave across a surface of a planar immersion lens in the incident medium, controlling a phase profile of the incident electromagnetic wave with the planar immersion lens to focus the incident electromagnetic wave into the refractive medium including wave components at or beyond a critical angle, and receiving the focused electromagnetic wave with a wireless power receiver disposed in the refractive medium.

In some embodiments, the critical angle is an angle of incidence above which total internal reflection in the incident medium would occur without the planar immersion lens.

In one embodiment, the refractive medium has a higher refractive index than the incident medium.

In some embodiments, the controlling step further comprises controlling an arbitrary phase profile on the incident electromagnetic wave by modulating the incident electromagnetic wave with sub-wavelength structures of the planar immersion lens.

In one specific embodiment, the sub-wavelength structures comprise a plurality of metallic strips and passive elements. In other embodiments, the passive elements comprise resistors, capacitors, and/or inductors.

In one embodiment, the receiving step further comprises receiving the focused electromagnetic wave with a coil of the wireless power receiver.

In another embodiment, the wireless power receiver has a diameter of 2 mm or less.

A planar immersion lens configured to focus electromagnetic radiation from an incident medium into a refractive medium is provided, comprising a substrate, a plurality of metallic elements disposed on the substrate, wherein adjacent metallic elements are separated by a sub-wavelength distance, and a plurality of passive elements disposed on the plurality of metallic elements, the planar immersion lens being configured to impart a phase profile on an incident electromagnetic wave passing across the planar immersion lens to focus the incident electromagnetic wave into the refractive medium with wave components at or beyond a critical angle.

In some embodiments, the critical angle is an angle of incidence above which total internal reflection in the incident medium would occur without the planar immersion lens.

In one embodiment, the refractive medium has a higher refractive index than the incident medium.

In some embodiments, the controlling step further comprises controlling an arbitrary phase profile on the incident electromagnetic wave by modulating the incident electromagnetic wave with sub-wavelength structures of the planar immersion lens.

In one specific embodiment, the sub-wavelength structures comprise a plurality of metallic strips and passive elements. In other embodiments, the passive elements comprise resistors, capacitors, and/or inductors.

In some embodiments, the metallic elements comprise copper.

In another embodiment, the planar immersion lens is configured to focus the incident electromagnetic wave having a wavelength $\lambda$ into the refractive material having a refractive index n, to a focal point having a size proportional to $\lambda/n$.

In some embodiments, the substrate is flexible and conformable to nonplanar surfaces.

In other embodiments, a wavelength $\lambda$ of the incident electromagnetic wave is in the radio-frequency region, in the infrared region, in the visible region, or in the ultraviolet region.

A wireless power transfer system is provided, comprising a planar immersion lens configured to focus electromagnetic radiation from an incident medium into a refractive medium, the planar immersion lens having, a substrate, a plurality of metallic elements disposed on the substrate, wherein adjacent metallic elements are separated by a sub-wavelength distance, and a plurality of passive elements disposed on the plurality of metallic elements, the planar immersion lens being configured to impart a phase gradient on an incident electromagnetic wave passing across the planar immersion lens to focus the incident electromagnetic wave into the refractive medium at or beyond a critical angle, and a wireless power receiver comprising an energy harvesting structure, the wireless power receiver being configured to receive the focused electromagnetic wave from the planar immersion lens with the energy harvesting structure to generate power in the wireless power receiver.

In some embodiments, the critical angle is an angle of incidence above which total internal reflection in the incident medium would occur without the planar immersion lens.

In other embodiments, the refractive medium has a higher refractive index than the incident medium.

In some embodiments, the planar immersion lens is configured to impart the phase gradient on the incident electromagnetic wave by modulating the incident electromagnetic wave with the metallic elements and passive elements of the planar immersion lens.

In one embodiment, the passive elements comprise resistors, capacitors, and/or inductors.

In other embodiments, the metallic elements comprise copper.

In one embodiment, the planar immersion lens is configured to focus the incident electromagnetic wave having a wavelength $\lambda$ into the refractive material having a refractive index n, to a focal point having a size proportional to $\lambda/n$.

In some embodiments, the substrate is flexible and conformable to nonplanar surfaces.

A method for focusing electromagnetic radiation from an incident medium into a refractive medium is provided, comprising the steps of generating an electromagnetic wave with a surface of a planar immersion lens disposed in the incident medium, and controlling a phase profile of the electromagnetic wave with the planar immersion lens to focus the incident electromagnetic wave into the refractive medium including wave components at or beyond a critical angle.

A planar immersion lens configured to focus electromagnetic radiation from an incident medium into a refractive medium is provided, comprising a substrate, a plurality of metallic elements disposed on the substrate, wherein adjacent metallic elements are separated by a sub-wavelength distance, a plurality of passive elements disposed on the plurality of metallic elements, and electronics coupled to the plurality of metallic elements and/or the passive elements and configured to excite the metallic elements and/or the passive elements to generate an electromagnetic wave, the planar immersion lens being configured to impart a phase profile on the electromagnetic wave to focus the incident electromagnetic wave into the refractive medium including wave components at or beyond a critical angle.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
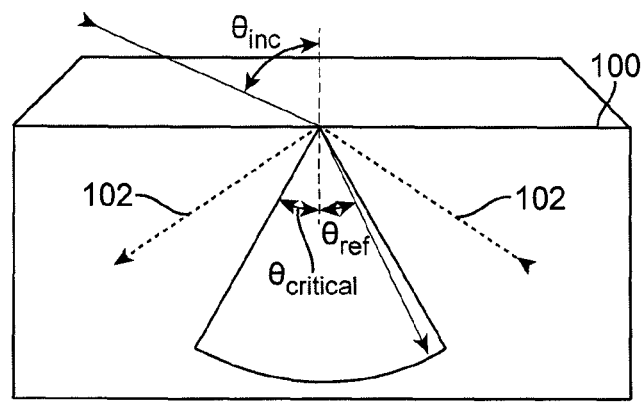
FIGS. 1A-1C illustrate a schematic of refraction at forbidden angles, showing ordinary refraction between air and material, and refraction at a forbidden angle using both an solid immersion lens and a metasurface-based planar lens.

The present disclosure describes techniques for creating and using planar immersion lenses: flat structures configured to strongly focus electromagnetic radiation from one material such as air into another material such as tissue. When illuminated by incident radiation or directly electronically excited, the structure sets up an evanescent field with a designed phase profile. In close proximity to material, the evanescent field couples into the material with the high-wave-vector components necessary to produce a subwavelength ($\sim\lambda/n$) focal spot by interference.

The planar immersion lenses described herein are based on metasurfaces, i.e., are structured at the subwavelength scale (termed "metasurfaces") to provide an abrupt change in electromagnetic properties across the surface. Their properties can be tuned by varying the parameters of the individual subwavelength elements to form a desired spatially varying response. Their design involves multiple steps: First, the phase profile needed to achieve focus at a prescribed depth in material is determined. Second, subwavelength elements with the necessary spatial resolution are set. Third, the reactive loads on individual elements are found for a specific mode of excitation.

Specific examples of planar immersion lenses in the radio-frequency regime are provided. These techniques can be implemented across the electromagnetic spectrum, including millimeter-waves, terahertz radiation, and infrared/visible light.

Certain aspects of the present disclosure are also directed toward implantable devices that receive power transmitted by planar immersion lenses that create a focused electromagnetic field from one material into another material having a higher refractive index. The implantable device, consistent with various aspects of the present disclosure, can be a size such that the device is deliverable via a catheter, cannula, or a needle. Additionally, the implantable device(s) can include a structure that receives the energy from the focused electromagnetic field. In such an embodiment, the energy carried by the field is received by an electrically or magnetically polarizable coil or wire. Further, the implantable devices can also include, in certain instances, a multi-turn coil that receives the focused energy, rectifying circuitry that converts the electromagnetic signal using AC-DC power conversion, and control circuitry to regulate pulse amplitudes, duration, and frequency.

Various aspects of the present disclosure are directed toward powering of one or more active implantable sensors or devices using a single power source. The types of implantable devices/sensors that can be powered using the single power source, consistent with various aspects of the present disclosure, are numerous. For instance, the implantable devices can be used for muscular stimulation, stimulation/sensing to regulate a patient's heart beat, multisite deep brain stimulation, drug delivery, and/or biological, physiological, and chemical sensing.

The devices disclosed herein can be individually addressable and independently controlled. Thus, the devices, for example as those used for muscular stimulation, can be placed at different locations corresponding to different muscle groups, and perform stimulation in a synchronized manner. Similarly, brain stimulation devices can be placed at different locations in the brain, and stimulation can be performed in a synchronized manner. The same can be said with drug delivery devices. Moreover, because the devices can be individually addressable and independently controlled, the devices can be activated and/or powered asynchronously as well as synchronously. These devices, in certain instances, can have characteristics dimensions in that the devices are much smaller (e.g., one, two, or three orders of magnitude) than their depth in tissue. Similarly, the devices, in certain instances, can have characteristics dimensions in that the devices are much smaller (e.g., one, two, or three orders of magnitude) than the source that provides the power to the devices.

Implantable devices/sensors can be wirelessly powered by controlling and propagating electromagnetic waves in tissue. The implantable devices can be implanted in humans or in other animals such as pets, livestock, or laboratory animals such as mice, rats, and other rodents. Such implantable devices/sensors can be implanted at target locations in a patient, as non-limiting examples, to stimulate areas such as the heart, and/or to sense biological, physiological, chemical attributes of the blood, tissue, and other patient aspects. Difficulties in achieving wireless power transfer can occur in the mismatch between the size of the implantable devices/sensors and the power transfer source, the depth of the devices/sensors in a patient, and additionally the spatial arrangement of the devices/sensors relative to the power transfer source.

Various aspects of the present disclosure are directed toward apparatuses or methods as exemplified or supported by aspects of the above noted description/embodiments, as well as the description/embodiments of the attached appendices. For instance, certain embodiments of the present disclosure are directed to manipulation of evanescent fields outside a patient's tissue with planar immersion lenses to focus electromagnetic fields from air into biological tissue. A planar immersion lens generates fields that are evanescent in nature near the source. In contrast, in conventional wireless approaches using inductive coupling, the evanescent components outside tissue (near the source) remain evanescent inside tissue which does not allow for effective energy transport.

This disclosure provides embodiments for a wireless powering approach that integrates a planar immersion lens configured to transmit wireless power, and one or more implanted modules configured to receive wireless energy and transduce the energy to electrical, optical, thermal, or mechanical form. In some embodiments, the implanted module can be small enough to be delivered via a catheter or a hypodermic needle. For example, the implanted module can be as small as a few millimeters in diameter (2-3 mm) down to having diameters on the order of 100's of microns or less. Because the implanted modules are small, they can be injected into the targeted nerve or muscle region directly without the need for leads and extensions, to provide sensing and stimulation to the targeted nerve, muscle, or tissue region.

Figure 1B:
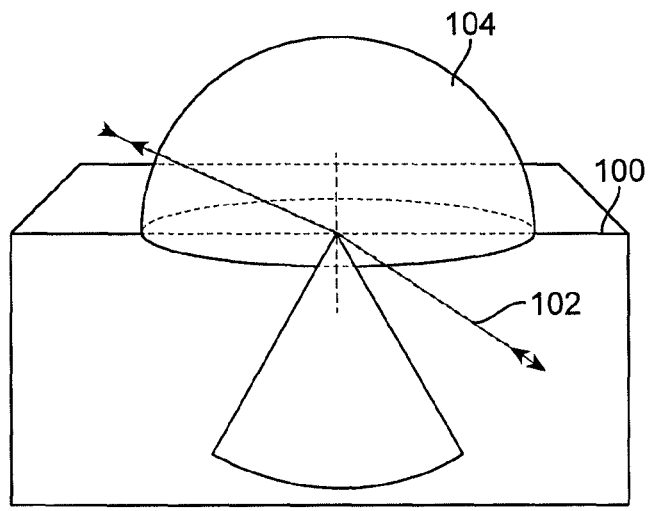

Refraction at forbidden angles, illustrated in FIG. 1A, is key to focusing incident radiation to a ~λ/n spot. FIG. 1A illustrates ordinary refraction, in which light cannot be refracted at an incident material/refractive material interface 100 beyond the critical angle $\theta_{critical}$ because the corresponding beam 102 is trapped by total internal reflection. For example, the incident material can comprise air and the refractive material can comprise biological tissue. The diffraction limit for focusing is set by the free-space wavelength ~λ. FIG. 1B shows refraction at an incident material/refractive material interface 100 with an immersion lens 104. The semispherical topography of the immersion lens 104 enables light to both enter and escape material at a forbidden angle shown by corresponding beam 102. Light can thus be focused to ~λ/n, where n is the material refractive index.

Figure 1C:
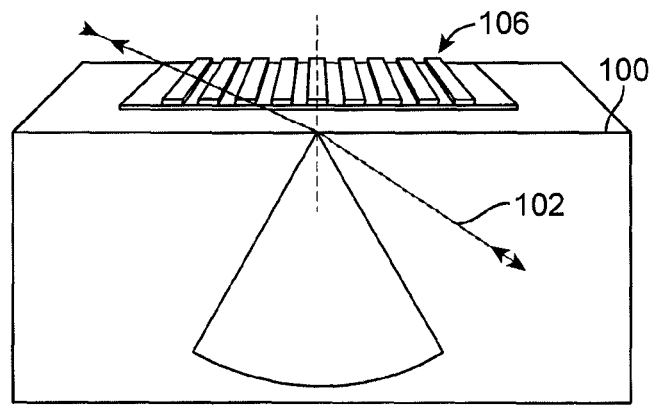

FIG. 1C shows refraction with a planar immersion lens 106 of the present invention, also be referred to as a metasurface, which is configured to change the amplitude and phase of electromagnetic waves propagating across its surface at an incident material/refractive material interface 100, thereby enabling the electromagnetic waves to refract at or beyond a forbidden angle such as the critical angle $\theta_{critical}$. The incident wave can be focused from one material (such as air) into another material having a higher refractive index (such as biological tissue). In some embodiments, the wavelength λ of the incident electromagnetic wave can be in the radio-frequency region, the infrared region, the ultraviolet region, or the visible region. The planar immersion lens 106 can implement a phase gradient on the incident electromagnetic waves by non-periodically modulating the surface with sub-wavelength structures of varying impedances. The planar immersion lens can also be directly excited, with electronics or other subwavelength sources, to generate a wave with the desired phase gradient, without requiring an existing incident wave. When the planar immersion lens 106 is not in contact with the incident material/refractive material interface 100, the incident waves can tunnel in and out of the material at or beyond the critical angle $\theta_{critical}$ as shown by beam 102. The focusing resolution of the planar immersion lens can therefore be the same as the immersion lens, without the substantial bulk of a conventional semispherical immersion lens.

Design Procedure: The planar immersion lenses of the present disclosure were designed by first solving for a field source in air that focuses to a λ/n spot in the material. Prior expressions for the optimal field source consider only far-field light and yield a ~λ focal spot. The approach described herein starts by formulating an optimization problem over the space of current sheets $j_s$ in the source plane (taken to be z=0). The solution to the problem is defined to be the current sheet that maximizes a metric for the degree of focus. For present purposes, it can be assumed that the material is dissipative, allowing small but nonzero loss. The efficiency of work performed on the material as the focusing metric, $$\eta = \frac{\alpha''|E(r_f)|^2}{\int dr \, \epsilon'' |E(r)|^2},$$

where $r_f$ is the focal point, $\alpha''$ is the imaginary part of the polarizability of the object at the focal point, and $\epsilon''$ is the imaginary part of the material dielectric permittivity. The imaginary part of the polarizability of the object, a, can be set to be the polarizability of a "virtual" sphere centered at the focal point: the sphere has the same dielectric permittivity as the background material and can be made arbitrarily small (e.g., the diameter of a computational mesh unit).

Focusing is posed as an optimization problem maximizing η over the space of all current sheets. The relationship between E and $j_s$ is found using a Green's function relation. On doing so, the solution to the optimization problem reduces to that of choosing the largest eigenvalue of an operator expression. Numerical computation can be considerably accelerated by (i) selecting the plane-wave basis, which diagonalizes the Green's function operator for the multilayer geometry, and (ii) exploiting degeneracies due to azimuthal symmetry about the focal axis. The calculation reduces to inversion of dyads at each spatial frequency, without need to explicitly form the full system matrices. This inverse filtering process is closely related to time reversal and can be generalized to transparent media by allowing the material loss to asymptotically approach zero.

Figure 2A:
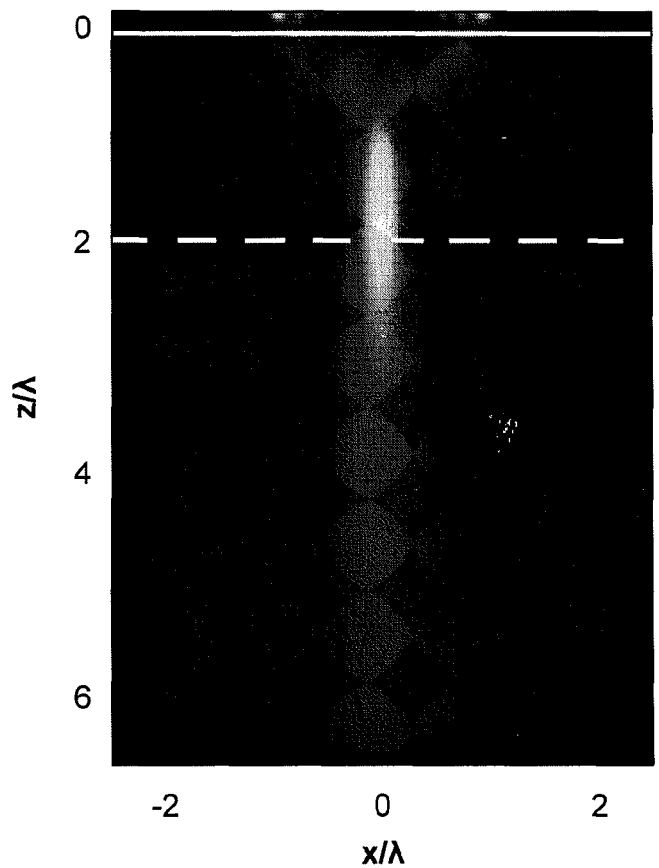
FIGS. 2A-2B illustrate subwavelength focusing of incident radiation from air into material.
Figure 2B:
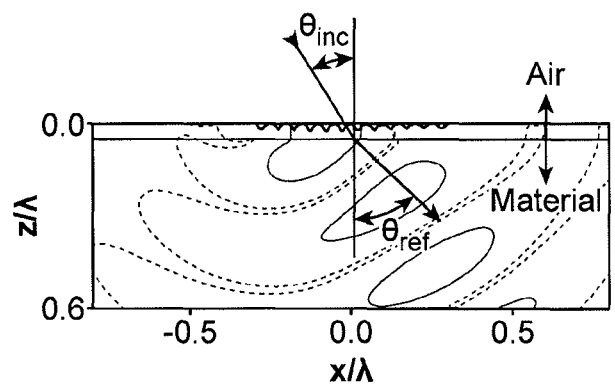

An example of refraction with a planar immersion lens in a two-dimensional geometry is shown in FIGS. 2A-2B where the material has a refractive index n=2. For incident s-polarized radiation, the source that focuses to a line at a 4 λ/n distance can be numerically solved for. A planar immersion lens 106 can be used to shape a normally incident plane wave such that the exiting field matches the solution. The required impedance values of the passive elements are solved by using a point-matching method. The linewidth of the focal spot is subwavelength 0.42λ full width at half maximum (FWHM). To verify that the focusing effect is due to phase (not amplitude) modulation of incident wave, the passive elements are removed such that the surface acts as a grated aperture. The focal spot for the grating is not subwavelength; the intensity at the focal point is also decreased by a factor of 4. FIG. 2B is another illustration showing refraction of incident waves at or beyond forbidden angles with a planar immersion lens, and illustrates magnetic field amplitude below the planar immersion lens in the air gap and material (n=2) with a plane wave at angle of incidence $\theta_{inc}$=30 deg. The angle of the refracted wave $\theta_{ref}$ is 45 deg as predicted by Snell's law. The refracted wave $\theta_{ref}$ is refracted with the planar immersion lens to an anomalous angle that lies well beyond the critical angle $\theta_{critical}$ of 30 deg.

Figure 3:
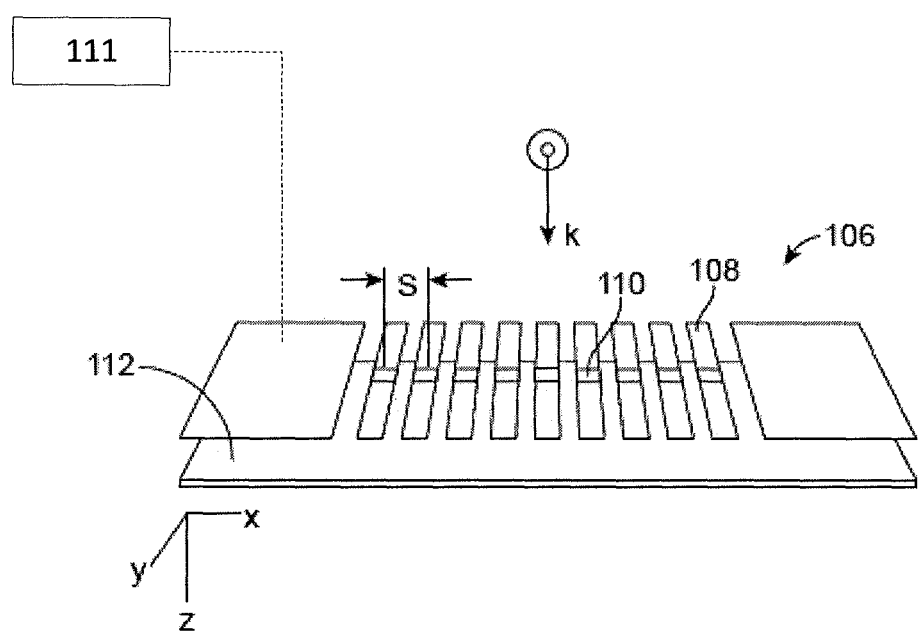
FIG. 3 illustrates one embodiment of a metasurface.
Figure 4A:
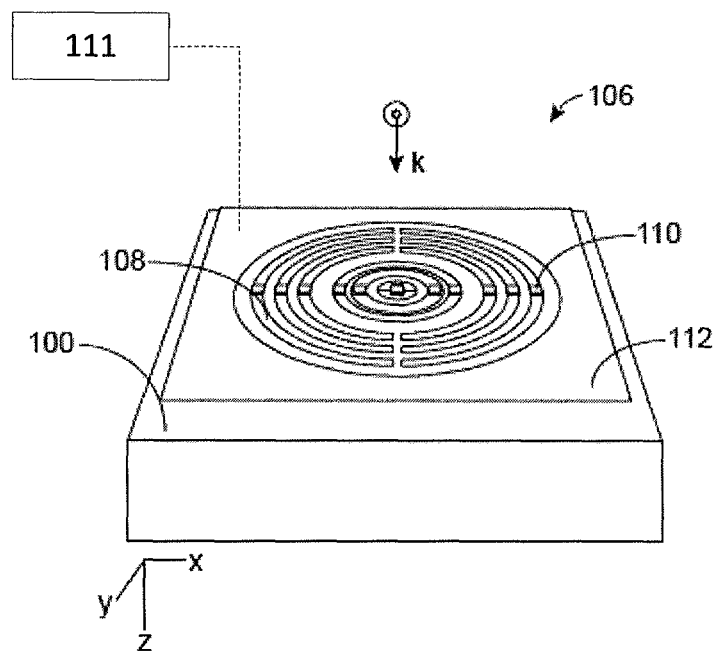
FIGS. 4A-4B illustrate another embodiment of a metasurface.
Figure 4B:
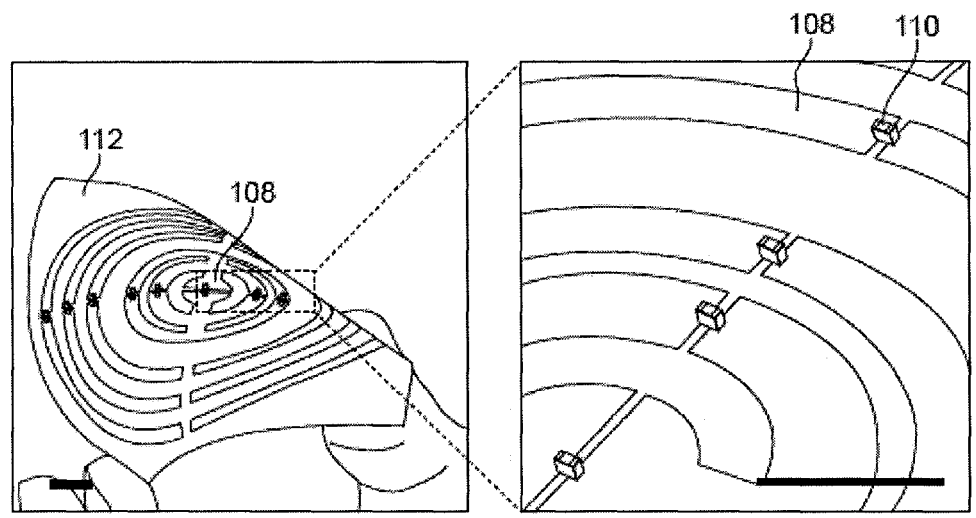

Example Device: FIGS. 3, 4A, and 4B show views of a planar immersion lens 106 according to various embodiments. The planar immersion lens 106 can be configured to control a phase profile of an incident wave k by non-periodically modulating the incident wave with sub-wavelength structures of varying impedances. In other embodiments, the planar immersion lens can also be directly excited, with electronics or other subwavelength sources 111 coupled to the planar immersion lens, to generate a wave with the desired phase gradient, without requiring an existing incident wave. The planar immersion lens 106 of both FIGS. 3 and 4A includes a plurality of metallic elements 108 and passive elements 110 disposed over a substrate 112. The passive elements can comprise resistors, capacitors, and/or inductors. The sets of metallic elements 108 and passive elements 110 can be separated from another by a sub-wavelength distance S. The metallic elements can comprise any metal, such as copper. In some embodiments, the metallic elements are arranged as strips of metal over the substrate 112. The passive elements can comprise, for example, ceramic capacitors and/or ferrite inductors. Across a resonance, the phase of the current in the metallic strips differs from that of a driving electric field by a value between 0 and π. The passive elements can be selected, based on both the intrinsic and mutual impedances of the elements, to shape the spatial phase profile of the incident wave within this phase range. The phase gradient can be introduced along the incident material/refractive material interface to focus the incident wave into the refractive material having wave components at or beyond the critical angle $\theta_{critical}$. This phase range can be extended to the full 0 to $2\pi$ by incorporating elements with a magnetic response, or cascading multiple layers of planar immersion lenses, each layer comprising a plurality of metallic strips and passive elements as shown in the embodiment of FIG. 3.

The embodiment of FIG. 3 shows a planar immersion lens 106 with a generally rectangular shape, having a plurality of metallic elements 108 arranged as parallel strips over a substrate 112. Each of the metallic elements can have a passive element 108 disposed thereon. The metallic elements, and therefore the passive elements, can be separated from adjacent metallic/passive elements by a sub-wavelength distance S. The embodiment of FIGS. 4A-4B shows a planar immersion lens 106 with a generally circular shape, in which the plurality of metallic elements 108 are arranged in generally concentric strips about a central element. The passive elements 110 are disposed on each of the metallic elements. In both embodiments, the planar immersion lens is generally planar. It should be understood that planar immersion lenses according to the present invention can include any size, shape, and any number of metallic elements and passive elements. FIG. 4B shows that the planar immersion lens 106 can be flexible, and further shows a zoomed-in view of the planar immersion lens including a closer view of the metallic strips 108 and passive elements 110 of the planar immersion lens.

Due to symmetry about the focal axis, the polarization of the fields at the focal point of the planar immersion lens can be arbitrarily specified. Setting the electric field to be linearly polarized in the x direction, the source is found to be a surface wave consisting of concentric ringlike currents around the focal axis. In air, the resulting fields are evanescent and nonstationary, propagating in-plane towards the focal axis. Importantly, the intensity profile at the source plane is significantly nonzero only within a finite circular region. The radius of this region defines an effective aperture size that is directly related to the loss in the material system and the depth of focus. Although the wave originates in air, the spot size approaches Abbe's diffraction limit $\lambda/(2 n \sin \theta_{ap})$ in homogenous material, where $\theta_{ap}$ is the half-angle the aperture subtends the focal point, due to the source's ability to access forbidden wave components.

Device Fabrication. As described above, a planar immersion lens according to the present invention is capable of focusing an incident plane wave. FIGS. 4A and 4B show an embodiment of the lens comprising of concentric metallic strips or rings loaded with passive elements forming an aperture. In agreement with time-reversal considerations, the phase response of the lens is parabolic with concavity reversed from that expected of an outward propagating wave. In some specific embodiments, the planar immersion lens 106 of FIGS. 4A-4B can provide for a lens that focuses an incident plane wave to a spot of size of $\lambda/8$ FWHM.

The concentric rings shown in FIGS. 4A-4B can be placed in a circular aperture of a chosen diameter. In one specific embodiment, the diameter of the concentric rings can be 8.4 cm, and the largest ring can have a diameter of 7.5 cm. To calculate the impedance values of the passive elements, a multiport simulation of the structure is performed. The required passive elements can then be obtained by solving a set of balance equations in the impedance matrix.

Wireless Powering with the Device. In the microwave regime, an application for the planar immersion lenses described herein is wireless energy transfer through biological tissue. Since tissue exhibits a relatively large refractive index at gigahertz frequencies (for example, real part of 7.4 for muscle at 1.6 GHz), the efficiency of energy transfer can be substantially enhanced if the focal spot size can approach $\sim\lambda/n$. In this context, the planar nature of planar immersion lenses is a key advantage because it enables fabrication on flexible substrates. The currents in the rings can be set up by applying an electric dipole moment across the central passive element such that the lens can be excited through a compact electronic source rather than an incident plane wave.

Figure 5:
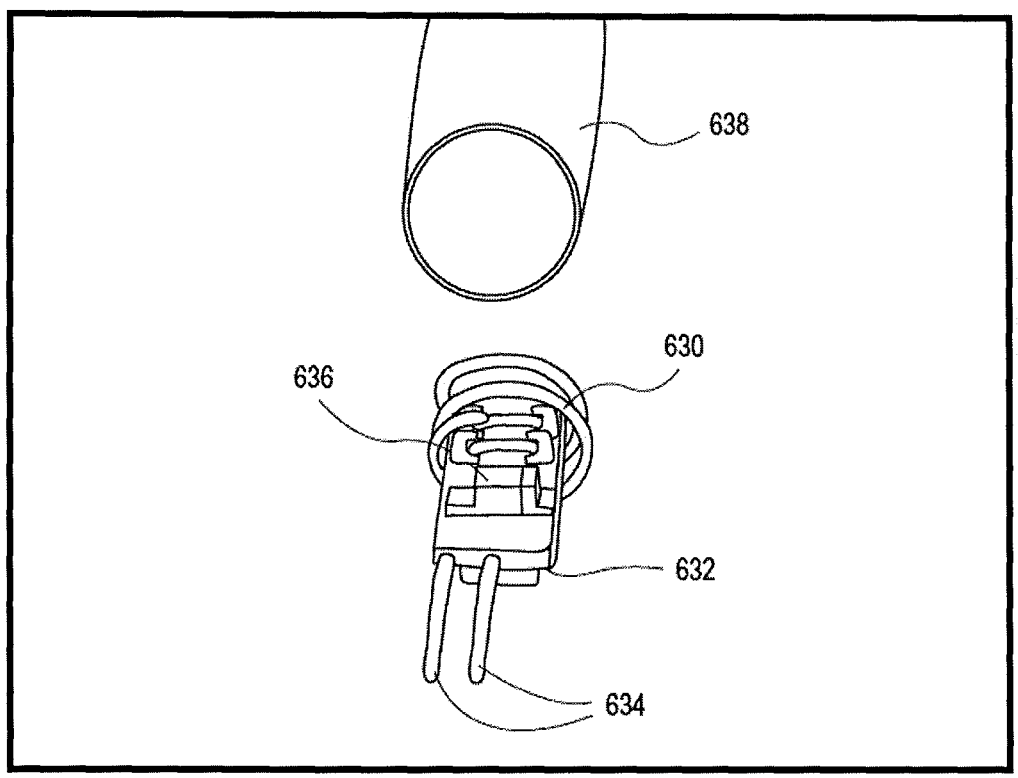
FIG. 5 shows one embodiment of an implantable device configured to receive wireless power from a metasurface.

Energy at the focal point of the planar immersion lens can be harvested with an implanted module having an energy harvesting structure. An example is shown in FIG. 5. The implanted module can include a coil 630 disposed over an integrated chipset (IC) 632. The coil 630 can be a loop (or multiple loops) of a conductor. In some embodiments, the coil 630 has a diameter of less than 2 mm. The coil can be configured to receive the wireless power transmitted from the external modules described herein. The module can optionally include features 634 for sensing and/or stimulating tissue, such as electrode(s) or sensors. The electrodes can comprise, for example, screw-type electrodes, planar electrodes, or cuff electrodes. In other embodiments, the sensors can comprise biopotential sensors, pressure sensors, O2 sensors, etc. The implanted module can optionally include electrical components for the storage of energy, such as a capacitor or battery 636. Due to the small size of the implanted module (2 mm or less in diameter), the implanted module can be delivered and implanted into a patient with minimally invasive techniques, such as with a catheter 638, a cannula, a needle, or the like.

Implantable devices and/or sensors such as the implanted module of FIG. 5 can be wirelessly powered by controlling and propagating electromagnetic waves in biological tissue. Such implantable devices/sensors can be implanted at target locations in a patient, as non-limiting examples, to stimulate areas such as the heart, and/or to sense biological, physiological, chemical attributes of the blood, tissue, and other patient aspects. Difficulties in achieving wireless power transfer can occur in the mismatch between the size of the implantable devices/sensors and the power transfer source, the depth of the devices/sensors in a patient, and additionally the spatial arrangement of the devices/sensors relative to the power transfer source.

The shape/distribution of the electromagnetic field can be tailored by varying the values of the passive components (inductances and/or capacitances) on the planar immersion lens. For example, the position of the focal spot can be moved both laterally and in depth in order to power implantable modules at different locations. This spatial adaptation of the electromagnetic field can be controlled physically, such as by stretching or bending the device, or electronically, using microcontrollers or application-specific integrated circuits. The electromagnetic field can be reconfigured many times a second. This enables the planar immersion lens to, for example, track movements of implanted modules on/near moving organs.

The implantable module can be used with sensors/devices that include feedback to the planar immersion lenses. These types of sensors can include, for example, implantable temperature sensors or imaging devices. In this manner, the devices are responsive to the structures illustrated above that generate a spatially adaptable electromagnetic field/signal.

The feedback-type devices respond to the power and/or data portions of the signal provided by the spatially adaptable electromagnetic field/signal, and are prompted to respond. For instance, temperature sensors located in a patient will broadcast/report the temperature of the tissue in response to the power and/or data portions of the signal provided by the spatially adaptable electromagnetic field/signal. Additionally, imaging devices implanted in a tissue can broadcast/report the captured images in response to the power and/or data portions of the signal provided by the spatially adaptable electromagnetic field/signal. Moreover, the penetration depth of the spatially adaptable electromagnetic field/signal can be modeled and controlled. Thus, in certain embodiments, the feedback devices can indicate and label data, in response to the spatially adaptable electromagnetic field/signal, to record the depth at which the device is operating. By storing this data on a patient-by-patient basis in a storage device, a computer can access and analyze this data for statistical purposes.

At optical frequencies, planar immersion lenses could be implemented with closely spaced plasmonic antennas or dielectric resonators, with mutual interactions accounted for by tuning the properties of optical "lumped" elements. By incorporating subwavelength structures that interact with the magnetic field component of incident radiation, the planar immersion lens could also modify the optical impedance, allowing reflection at the interface to be eliminated.

The simple and planar nature of the described device has direct application in nanophotonic chips, for strongly focusing light from one material into another, and conformal biomedical devices, for manipulating radio-frequency radiation in and near the human body. Applications such as lithography, data storage, and microscopy may be employed because of the high resolution that can be obtained. For example, a planar immersion lens of the present disclosure can be used to improve resolution of features. In a nanophotonics application, a planar immersion lens can be applied for confinement of light. The planar immersion lens can also be used in communication applications to enable radio waves to pass through and focus into different material environments.

The wave incident on the planar immersion lens can originate from any radiative source. At radio-frequencies, these sources can, for example, comprise antennas, phased-arrays, or cavity resonators. At optical frequencies, the sources can be lasers, light-emitting diodes, or light filaments. The planar immersion lens can also be excited directly using electronics or other subwavelength sources. For instance, a radio-frequency oscillator can be used to induce oscillatory currents across surface of the lens with defined relative phases. The field emanating from these currents can be strongly focused in material.

The planar immersion lens can be used, in some embodiments, to wirelessly transfer electromagnetic energy into the body for therapeutic effect or for powering electronic devices.

Various aspects of the present disclosure are directed toward powering of multiple active implantable sensors or devices using a single planar immersion lens. The types of implantable devices/sensors that can be powered using the single planar immersion lens, consistent with various aspects of the present disclosure, are numerous. For instance, the implantable devices can be used for muscular stimulation, stimulation/sensing to regulate a patient's heart beat, multisite deep brain stimulation, drug delivery, and/or biological, physiological, and chemical sensing.

Moreover, because the devices can be individually addressable and independently controlled, the devices can be activated and/or powered asynchronously as well as synchronously. These devices, in certain instances, can have characteristics dimensions in that the devices are much smaller (e.g., one, two, or three orders of magnitude) than their depth in tissue. Similarly, the devices, in certain instances, can have characteristics dimensions in that the devices are much smaller (e.g., one, two, or three orders of magnitude) than the source that provides the power to the devices.

Methods of use are also provided, including:

A method for focusing electromagnetic radiation from an incident medium into a refractive medium is provided, comprising the steps of generating an incident electromagnetic wave across a surface of a planar immersion lens in the incident medium, and controlling a phase profile of the incident electromagnetic wave with the planar immersion lens to focus the incident electromagnetic wave into the refractive medium including wave components at or beyond a critical angle.

In some embodiments, the critical angle is an angle of incidence above which total internal reflection in the incident medium would occur without the planar immersion lens.

In one embodiment, the refractive medium has a higher refractive index than the incident medium.

In some embodiments, the controlling step further comprises controlling an arbitrary phase profile on the incident electromagnetic wave by modulating the incident electromagnetic wave with sub-wavelength structures of the planar immersion lens.

In one specific embodiment, the sub-wavelength structures comprise a plurality of metallic strips and passive elements. In other embodiments, the passive elements comprise resistors, capacitors, and/or inductors.

A method for transmitting wireless power from an incident medium into a refractive medium is provided, comprising the steps of generating an incident electromagnetic wave across a surface of a planar immersion lens in the incident medium, controlling a phase profile of the incident electromagnetic wave with the planar immersion lens to focus the incident electromagnetic wave into the refractive medium including wave components at or beyond a critical angle, and receiving the focused electromagnetic wave with a wireless power receiver disposed in the refractive medium.

In some embodiments, the critical angle is an angle of incidence above which total internal reflection in the incident medium would occur without the planar immersion lens.

In one embodiment, the refractive medium has a higher refractive index than the incident medium.

In some embodiments, the controlling step further comprises controlling an arbitrary phase profile on the incident electromagnetic wave by modulating the incident electromagnetic wave with sub-wavelength structures of the planar immersion lens.

In one specific embodiment, the sub-wavelength structures comprise a plurality of metallic strips and passive elements. In other embodiments, the passive elements comprise resistors, capacitors, and/or inductors.

In one embodiment, the receiving step further comprises receiving the focused electromagnetic wave with a coil of the wireless power receiver.

In another embodiment, the wireless power receiver has a diameter of 2 mm or less.

A method for focusing electromagnetic radiation from an incident medium into a refractive medium is provided, comprising the steps of generating an electromagnetic wave with a surface of a planar immersion lens disposed in the incident medium, and controlling a phase profile of the electromagnetic wave with the planar immersion lens to focus the incident electromagnetic wave into the refractive medium including wave components at or beyond a critical angle.

A planar immersion lens configured to focus electromagnetic radiation from an incident medium into a refractive medium is provided, comprising a substrate, a plurality of metallic elements disposed on the substrate, wherein adjacent metallic elements are separated by a sub-wavelength distance, a plurality of passive elements disposed on the plurality of metallic elements, and electronics coupled to the plurality of metallic elements and/or the passive elements and configured to excite the metallic elements and/or the passive elements to generate an electromagnetic wave, the planar immersion lens being configured to impart a phase profile on the electromagnetic wave to focus the incident electromagnetic wave into the refractive medium including wave components at or beyond a critical angle.

The system of the present disclosure allows for the transfer of substantial amount of power to small implanted modules at nearly any location in the body from a thin planar immersion lens. This enables new sensing applications for continuous monitoring and control of physiological parameters for many applications.

Cardio pacemaker. The implanted module can be delivered via a catheter through the vasculature into the right ventricle of a patient. A separate implanted module can be delivered through the coronary sinus into the coronary vein, and placed on the left ventricular epicardium. These implanted modules can include stimulation and sensing electrodes to apply leadless pacing to the heart. Thus, leadless biventricular pacing can be achieved with the present system with only minimally invasive procedures. In addition, the procedure time can be shortened substantially over prior approaches. This can also eliminate any complication during to the multiple leads and extensions.

Deep-brain stimulation. Current procedure involves the drilling of holes with diameter >1 cm in the skull to insert a lead and the extension from the lead to the stimulating module. Due to the invasiveness of the procedure, only a limited number of target sites are selected for placing the electrodes. By contrast, the implanted modules in this disclosure, being very small, can be injected into the brain via other less invasive routes. Since there is no lead and extension wire in the present system, more target sites for stimulation can be supported. This results in less infection and lower regulatory risk.

Spinal cord stimulation. Batteries in newer models of spinal cord stimulator are rechargeable due to the high power requirement. However, their powering approaches are exclusively based on inductive coupling (or near-field coupling). Since the harvesting components are large in these systems, they can only be placed subcutaneously. Therefore, the lead and extension wires in these systems potentially restrict the location of the electrodes for effective stimulation. In this disclosure, the power-harvesting component in the implanted module is relatively tiny. The entire implanted module can be easily placed next to the targeted nerve region in the spinal cord and requires no lead wire connecting them. This results in less infection, less damage to the spinal cord tissue, and more effective stimulation.

Peripheral nerve stimulation. Most current devices support low-frequency stimulation and only a few of them support high-frequency low-intensity stimulation due to the much higher power requirement. The systems of this disclosure can support both modes. In addition, the bidirectional wireless link provides instant programmability, switching between different modes.

Stimulation to treat obstructive sleep apnea (OSA). The implanted modules of this disclosure can be injected and directly embedded into the muscular tissue near the tongue, and can deliver electrical stimulation to open the airway of a patient during sleep. Multiple implant modules can be injected into different muscular groups to intensify the muscle contraction. When needed, patients can charge the implanted modules with the external module and simultaneously, download a time stamp of each OSA episode. This information can be sent to the clinicians. Data collected can also be used to reprogram the implanted modules.

Medical sensors. Batteryless implanted sensors are typically passive in nature, that is, there is no active circuitry in the device to condition the sensed signals. To compensate for the poor signal quality, an external reader is needed to be very sophisticated and is usually large (cannot be fitted on a palm). In addition, not many stimuli can be detected by passive sensors. The lack of active implanted sensors is mainly due to the lack of an efficient wireless powering approach. For example, the inductive coupling approach used in the rechargeable impulse generator for spinal cord stimulation has limited penetration and the receiver (the implanted device) is large. The system of the present disclosure allows for the transfer of substantial amount of power to small implanted modules at nearly any location in the body from a palm-size external module. This enables an array of new sensing applications for continuous monitoring in the medical field, for example, post-surgery oxygen sensing in the heart and the brain.

Wireless endoscopes. Current capsule endoscope has limited battery lifetime, leading to incomplete small-bowel examination which is one of the major clinical failures. The implant module in our invention is small and has indefinite power supply, solving the deficiency of current endoscopes. In addition, since our implant module is many times smaller than the current capsule endoscope, patients can swallow multiple of the implant modules simultaneously. They are expected to orient differently in the intestine and therefore, can take pictures from different angles at the same location, improving the field of view. The images collected from them will improve the diagnosis. Finally, the probability of retention is expected to be dramatically reduced, avoiding the need of surgical or endoscopic retrieval.

Implanted drug delivery. Current implanted drug delivery systems are large and mostly cannot be placed local to the site that the drug is needed. Based on this disclosure, the implanted module can be injected into a targeted tissue region (for example, a tumor) where the drug is needed. The implanted module can include a number of drug reservoirs. The drug reservoirs can be activated by the external module via the patient/clinician user interface to release a drug into the targeted tissue region.

Temporary treatment. Currently, screening tests are typically performed before a permanent impulse generator is implanted. During the screening test, a patient may receive a temporary, external impulse generator. The generator can connect to an extension and a lead that are surgically placed in the body. In this period, the external impulse generator collects patient usage data and efficacy of the treatment. However, according to this disclosure, the implanted module having an electrode and an impulse generator can be injected into the targeted nerve/muscle region, eliminating the need for a temporary generator with leads. There is therefore no need for the external temporary impulse generator. In addition, this disclosure can also replace the temporary sensing and pacing leads used in patients after cardiac surgery.

Laboratory Experiments. The implanted module can be injected into lab animals or rodents (such as mice, rats, etc.) to monitor or sense parameters of the animal and/or provide stimulation to the animal in an experimental setting. The small size of the implanted module can advantageously provide opportunities to monitor the animal that has not been previously available. For example, the implanted module could be implanted on or near the brain of a rodent to monitor electrical signals of the brain. The implant can be wirelessly powered with the external module described above, and can be configured to communicate information back to the external module relating to the animal.

While the present disclosure (which includes the attachments) is amenable to various modifications and alternative forms, specifics thereof have been shown by way of example in the drawings and will be described in further detail. It should be understood that the intention is not to limit the disclosure to the particular embodiments and/or applications described. Various embodiments described above and shown in the figures and attachments may be implemented together and/or in other manners. One or more of the items depicted in the drawings/figures can also be implemented in a more separated or integrated manner, as is useful in accordance with particular applications.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method for focusing electromagnetic radiation from an incident medium into a refractive medium, comprising the steps of:
   generating an incident electromagnetic wave across a surface of a planar immersion lens in the incident medium; and
   controlling a phase profile of the incident electromagnetic wave by modulating the incident electromagnetic wave with sub-wavelength structures of the planar immersion lens, wherein the sub-wavelength structures comprise a plurality of metallic strips and a plurality of passive elements disposed on the plurality of metallic strips, wherein controlling the phase profile of the incident electromagnetic wave is configured to focus the incident electromagnetic wave across an air-gap between the planar immersion lens and the refractive medium including wave components at or beyond a critical angle.

2. The method of claim 1, wherein the critical angle is an angle of incidence above which total internal reflection in the incident medium would occur without the planar immersion lens.

3. The method of claim 1, wherein the refractive medium has a higher refractive index than the incident medium.

4. The method of claim 1, wherein the passive elements comprise resistors, capacitors, and/or inductors.

5. The method of claim 1, further comprising receiving the focused electromagnetic wave with a wireless power receiver disposed in the refractive medium.

6. The method of claim 5, wherein the receiving step further comprises receiving the focused electromagnetic wave with a coil of the wireless power receiver.

7. The method of claim 5, wherein the wireless power receiver has a diameter of 2 mm or less.

8. A planar immersion lens configured to focus electromagnetic radiation from an incident medium into a refractive medium, comprising:
   a substrate;
   a plurality of metallic elements disposed on the substrate, wherein adjacent metallic elements are separated by a sub-wavelength distance; and
   a plurality of passive elements disposed on the plurality of metallic elements;
   the planar immersion lens being configured to impart a phase profile on an incident electromagnetic wave passing across the planar immersion lens to focus the incident electromagnetic wave across an air-gap between the planar immersion lens and the refractive medium with wave components at or beyond a critical angle.

9. The planar immersion lens of claim 8, wherein the critical angle is an angle of incidence above which total internal reflection in the incident medium would occur without the planar immersion lens.

10. The planar immersion lens of claim 8, wherein the refractive medium has a higher refractive index than the incident medium.

11. The planar immersion lens of claim 8, wherein the planar immersion lens is configured to impart the phase profile on the incident electromagnetic wave by modulating the incident electromagnetic wave with the metallic elements and passive elements of the planar immersion lens.

12. The planar immersion lens of claim 8, wherein passive elements comprise resistors, capacitors, and/or inductors.

13. The planar immersion lens of claim 8, wherein the planar immersion lens is configured to focus the incident electromagnetic wave having a wavelength $\lambda$ into the refractive material having a refractive index n, to a focal point having a size proportional to $\lambda/n$.

14. The planar immersion lens of claim 8, wherein the substrate is flexible and conformable to nonplanar surfaces.

15. The planar immersion lens of claim 8, wherein a wavelength $\lambda$ of the incident electromagnetic wave is selected from the group consisting of the radio-frequency region, the infrared region, the visible region, and the ultraviolet region.

16. A wireless power transfer system, comprising:
a planar immersion lens configured to focus electromagnetic radiation from an incident medium into a refractive medium, the planar immersion lens having:
a substrate;
a plurality of metallic elements disposed on the substrate, wherein adjacent metallic elements are separated by a sub-wavelength distance; and
a plurality of passive elements disposed on the plurality of metallic elements;
the planar immersion lens being configured to impart a phase gradient on an incident electromagnetic wave passing across the planar immersion lens to focus the incident electromagnetic wave across an air-gap between the planar immersion lens and the refractive medium at or beyond a critical angle; and
a wireless power receiver comprising an energy harvesting structure, the wireless power receiver being configured to receive the focused electromagnetic wave from the planar immersion lens with the energy harvesting structure to generate power in the wireless power receiver.

17. The wireless power transfer system of claim 16, wherein the critical angle is an angle of incidence above which total internal reflection in the incident medium would occur without the planar immersion lens.

\* \* \* \* \*